United States Patent
Efthimios

(10) Patent No.: US 11,439,584 B2
(45) Date of Patent: Sep. 13, 2022

(54) COMPLETE ANHYDROUS SUNSCREEN COMPOSITION WITH UNDER WATER TECHNOLOGY

(71) Applicant: FREZYDERM S.A., Athens (GR)

(72) Inventor: Anastasiou Efthimios, Heraklion Attikis (GR)

(73) Assignee: FREZYDERM S.A., Athens (GR)

( * ) Notice: Subject to any disclaimer, the term of this patent is extended or adjusted under 35 U.S.C. 154(b) by 0 days.

(21) Appl. No.: 15/551,230

(22) PCT Filed: Feb. 10, 2016

(86) PCT No.: PCT/EP2016/000233
§ 371 (c)(1),
(2) Date: Aug. 15, 2017

(87) PCT Pub. No.: WO2016/131532
PCT Pub. Date: Aug. 25, 2016

(65) Prior Publication Data
US 2018/0015022 A1    Jan. 18, 2018

(30) Foreign Application Priority Data
Feb. 16, 2015   (EP) .................... 15 075 008

(51) Int. Cl.
| | | |
|---|---|---|
| *A61K 8/895* | (2006.01) | |
| *A61K 8/25* | (2006.01) | |
| *A61K 8/894* | (2006.01) | |
| *A61Q 17/00* | (2006.01) | |
| *A61K 8/31* | (2006.01) | |
| *A61K 8/41* | (2006.01) | |
| *A61Q 17/04* | (2006.01) | |

(52) U.S. Cl.
CPC ............. *A61K 8/895* (2013.01); *A61K 8/25* (2013.01); *A61K 8/31* (2013.01); *A61K 8/415* (2013.01); *A61K 8/894* (2013.01); *A61Q 17/00* (2013.01); *A61Q 17/04* (2013.01); *A61K 2800/805* (2013.01)

(58) Field of Classification Search
CPC ................... A61K 8/895; A61Q 17/00
See application file for complete search history.

(56) References Cited

U.S. PATENT DOCUMENTS

| | | | | |
|---|---|---|---|---|
| 6,197,281 | B1 * | 3/2001 | Stewart ............... | A61K 8/06 424/401 |
| 2005/0158258 | A1 * | 7/2005 | Fisher ............... | A61K 8/361 424/63 |
| 2010/0061947 | A1 * | 3/2010 | Schlossman ......... | A61K 8/19 424/59 |
| 2010/0092408 | A1 | 4/2010 | Breyfogle et al. | |
| 2013/0230474 | A1 | 9/2013 | Tanner | |
| 2014/0010769 | A1 | 1/2014 | Lomakin et al. | |
| 2015/0272841 | A1 * | 10/2015 | Fascina ............... | A61K 8/25 424/59 |
| 2016/0120791 | A1 * | 5/2016 | Dersh ............... | A61K 8/894 424/59 |
| 2016/0158134 | A1 * | 6/2016 | Disalvo ............... | A61K 8/31 424/59 |
| 2017/0189293 | A1 | 7/2017 | Spaulding et al. | |

FOREIGN PATENT DOCUMENTS

| | | |
|---|---|---|
| GR | 1008246 B | 7/2014 |
| WO | WO 2010/045163 A2 | 4/2010 |
| WO | WO 2013/130948 A2 | 9/2013 |
| WO | WO 2013/158844 A2 | 10/2013 |
| WO | WO 2014/168773 A1 | 10/2014 |

OTHER PUBLICATIONS

"Dowsil EL-8050 ID Silicone Organic Elastomer Blend", Technical Data Sheet, 2019, Dow Chemical Company.*
Diffey, B., "When should sunscreen be reapplied?" 2001, J Am Acad Dermatol, vol. 45, No. 6, p. 882-885.*
Dow Corning 9701 Cosmetic Powder, Product Information, 2012, Dow Corning Corporation.*
International Search Report (PCT/ISA/210) dated Jun. 29, 2016, by the European Patent Office as the International Searching Authority for International Application No. PCT/EP2016/000233.
Written Opinion (PCT/ISA/237) dated Jun. 29, 2016, by the European Patent Office as the International Searching Authority for International Application No. PCT/EP2016/000233.
European Search Report dated Jun. 17, 2015 for European Application No. 15075008.

* cited by examiner

Primary Examiner — Gina C Justice
(74) Attorney, Agent, or Firm — Buchanan Ingersoll & Rooney PC

(57) ABSTRACT

The invention provides a 100% anhydrous sunscreen composition and a use of this sunscreen composition with very high water and sweat resistance properties which can be applied on a wet skin, either in the presence of water by repelling water or water droplets respectively or in under-water conditions. The present invention describes a sunscreen composition comprising a silicone organic elastomer blend comprising Dimethicone/Bis-Isobutyl PPG-20 Crosspolymer in Isododecane in a concentration range from about 30% to about 90% w/w and a silicone elastomer comprising Dimethicone/Vinyl Dimethicone Crosspolymer and Silica in a concentration range from about 0.1% to about 10% w/w. The sunscreen may be applied on the skin in the presence of water (in wet and/or under-water conditions). Further, the new sunscreen product allows the consumer to enter water directly after the application of the sunscreen product on his dry or already wet skin.

18 Claims, No Drawings

COMPLETE ANHYDROUS SUNSCREEN COMPOSITION WITH UNDER WATER TECHNOLOGY

CROSS REFERENCE TO RELATED APPLICATIONS

This application is the U.S. national stage of PCT/EP2016/000233, filed on Feb. 10, 2016, which claims the benefit of European Application No. 15075008.1, filed on Feb. 16, 2015.

FIELD OF THE INVENTION

Embodiments relate to the field of cosmetic products, in particular to the field of sunscreen compositions.

BACKGROUND OF THE INVENTION

Conventional Sunscreen products are well known to consumers and are widely spread in the market. It is known that for aesthetic reasons, most of the people desire to tan quickly during their summer vacations and to conserve this tanning (pigmentation) as long as possible. But prolonged sun exposure causes to the skin apart from 'redness' (erythema-burn) other damages that set human health in danger (skin cancer, dermal dyschromias, nevus appearance, malignant mutation of existing nevus etc.). For this reason, sunscreen products are being produced with high Sun Protection Factors (to reassure the very high protection of the health of the skin against the UV induced erythema and burn) and always in respect to the existing and latest Legislation standards (for the cosmetic products in general and more precisely for the Sun Protection Factor and the Water Resistance of the sunscreen products). The legislation standards may be EU but also USA or any other official ones.

Due to their synthesis, the typical known sunscreen products are greasy, heavy, not light, unmanageable and finally not preferred by the consumer, who rejects using them, setting his health under danger.

In the past this disadvantage could be solved with a novel anhydrous sunscreen product. GR1008246 discloses a water-free sunscreen product with an anhydrous formula which contains 100% oily and/or oil soluble ingredients. When applied topically to the skin the product provides a non-greasy feel, it has a very rapid spreadability, a complete transparency and zero stickiness by improving at the same time skin aspect (reduction of shine, optical reduction of fine lines and wrinkles).

But some other disadvantages still remain unresolved:
When applied to dry skin, conventional sunscreens often provide a successful and durable protective barrier. But when applied to wet skin the UV-filter compounds and/or UV-screening compounds are diluted, the product cannot be applied evenly on the skin; it smears and forms a white, pasty and incomplete film, which renders in an insufficient protection against UV-radiation. Thus the consumer needs to have dry skin, which is not feasible when consumers in the water/sea or is coming out of the water/sea or is doing water-sports or beach-sports (beach sports result in sweaty skin). The time needed for drying the skin is often sufficient enough to cause an erythema, sunburn or other damages of the skin.
Additionally, one of the consumers' usual practices is to keep their skin wet in order to avoid sun induced heating sensation and to prolong the cooling sensation of water. That's why they even prefer to apply their sunscreen product into water. Apart from not being feasible with the conventional sunscreen products, this practice can't be considered as environmentally friendly and/or conscious, as sea surface gets polluted with accumulated sunscreen products. Conventional sunscreen products, even when they claim to be water resistant and pass the official water resistance test, are not so well anchored onto the skin and a great part of them is being released into the sea leading to reduced skin protection and increased environmental burden.
Another fundamental disadvantage of the conventional sunscreens is that the consumer has to wait about 20 minutes after the application of the sunscreen product onto the skin before entering into water. These 20 minutes are essential for activating the sunscreen protection by strongly anchoring the product onto the skin and activating the water resistant agents of the formulations. In other words, these 20 minutes are necessary for the product to remain onto the skin and not get diluted when it gets in contact with the water.
Last but not least, another disadvantage of the conventional sunscreen products is that when the consumer applies it onto the skin, any toweling afterwards leads to its removal. The consumer should not towel himself following to the sunscreen application, something that could be considered as inconvenient.

The current conventional sunscreen formulations can be divided in 3 groups:
a. Those that are supposed to be applicable on wet skin but, in reality, they cannot provide sufficient anchoring and subsequently effective water resistance, as these products contain water because they are oil in water emulsions. With this type of sunscreen products, the dilution of the UV-filter or UV-screening compounds cannot be avoided.
b. Those that can be applied on wet skin without leaving white marks onto it, but they contain high amounts of ethyl alcohol (negative effect of ethyl alcohol is that it dries out the skin), and therefore it is strongly recommended to avoid their use on sensitive skin and face. Moreover these types of sunscreen products are very liquid and cannot be anchored on the skin leading to insufficient sun protection.
c. Those that cannot be applied on wet skin at all, because they are water in oil emulsions.

None of the above mentioned 3 groups can be applied safely and effectively on the skin in the presence of water, e.g. when the skin is under water or when the skin is already wet, by repelling water or water droplets. Moreover, none of the known products allow the consumer to enter the water/sea directly after the sunscreen product is applied on his either dry or wet skin.

BRIEF SUMMARY OF THE INVENTION

Embodiments herein are directed to an anhydrous sunscreen product and a method of protecting skin from sunlight comprising applying the anhydrous sunscreen product to skin. The anhydrous sunscreen product exhibits very high water and sweat resistance properties.

Embodiments may provide a 100% anhydrous sunscreen composition and a use of this sunscreen composition with very high water and sweat resistance properties which can be applied on a wet skin, either in the presence of water by repelling water or water droplets respectively or in underwater conditions. This sunscreen composition can be applied on dry skin as well.

In an embodiment, a composition comprises from about 30% to about 90% w/w of a silicone organic elastomer blend including Dimethicone/Bis-Isobutyl PPG-20 Crosspolymer and Isododecane; and from about 0.1% to about 10% w/w of a silicone elastomer including Dimethicone/Vinyl Dimethicone Crosspolymer and Silica.

In some embodiments, the composition comprises from about 55% to about 65% w/w of the silicone organic elastomer blend. In some embodiments, the composition comprises about 60.545% w/w of the silicone organic elastomer blend.

In some embodiments, the composition comprises from about 0.5% to about 1.5% w/w of the silicone elastomer. In some embodiments, the composition comprises about 1% w/w of the silicone elastomer.

In some embodiments, the silicone organic elastomer blend further includes cyclomethicone.

In some embodiments, the silicone organic elastomer blend further includes isohexadecane.

In some embodiments, the composition further comprises a UVA-filter and a UVB-filter.

In some embodiments, the composition further comprises at least one component selected from the group consisting of iron oxides, yellow 5 and titanium dioxide. In some embodiments, the group consisting of iron oxides, yellow 5 and titanium dioxide is selected from the group consisting of CI 77492, CI 77491, CI 77499 in *Ricinus communis* oil, CI 19140 in *Ricinus communis* oil, CI 77891 in *Ricinus communis* oil.

In some embodiments, the composition further comprises at least one pair of components selected from the group consisting CI 77499 and isopropyl titanium triisostearate; iron oxides CI 77492 and isopropyl titanium triisostearate; iron oxides CI 77491 and isopropyl titanium triisostearate; and titanium dioxide and isopropyl titanium triisostearate.

In some embodiments, the composition further comprises at least one ingredient selected from the group consisting of:
a) at least one emollient ester or other oily component, selected from a group consisting of dibutyl adipate, phenethyl benzoate, caprylic/capric triglyceride, C12-15 alkyl benzoate, PPG-3 benzyl ether myristate, C12-13 alkyl lactate, isodecyl salicylate, Di-C12-13 alkyl malate, isoamyl laurate, propylheptyl caprylate, butyloctyl salicylate, polycrylene, dicaprylyl carbonate, dicaprylyl ether, 2-octyldodecylmyristate, isohexadecane, dimethyl capramide, *Crambe abyssinica* oil, squalene, rice bran/germ oil, *Helianthus annuus* seed oil, *Ricinus communis* oil, dimethicone, cyclomethicone, caprylyl methicone, dimethicone copolyol undecylcrylene dimethicone, isopropyl isostearate, isostearyl isostearate, octyldodecanol, coca-glycerides, C13-15 Alkane, C15-19 Alkane, C17-23 Alkane, C21-28 Alkane, propylene glycol dipelargonate, diisopropyl sebacate, isononyl isononanoate, isocetyl stearoyl stearate, dipentaerithrityl hexacaprylate/hexacaprate, isodecyl neopentanoate, and natural essential oils;
b) at least one anti-aging ingredient, selected from the group consisting of ethyl ferulate, *Rosmarinus officinalis*, disodium uridine phosphate, polyglyceryl-5 trioleate, *Rosmarinus officinalis* extract, and *Helianthus annuus* seed oil;
c) at least one active ingredients, selected from the group consisting of a-bisabolol, *Crambe maritima, Bixa orellana*, retinyl palmitate, tocopheryl acetate, ascorbyl tetraisopalmitate, *Pistacia lentiscus* gum, *Salicornia herbacea* extract, *Rasa moschata* seed oil, teprenone, *Serenoa serrulate*, butyl avocadate, dipalmitoyl hydroxyproline, *Glycine soja* seed oil, ceramide-2, *Zea mays* oil, *Crambe abyssinica* seed oil phytosterol esters, *Echium plantagineum* seed oil, *Cardiospermum halicacabum* flower/leaf/vine extract, phytosphingosine, *Helianthus annuus* seed oil unsaponifiables, sodium caproyl/lauryl lactylate, triethyl citrate, *Salvia officinalis* oil, kojic acid dipalmitate, lecithin, arachidyl propionate, ethyl linoleate, ethyl linolenate, ethyl oleate, bakuchiol, *Juglans regia, Sesamum indicum* oil, *Triticum vulgare* germ oil, *Arnica montana, Cupressus sempervirens, Polygonatum multiflorum, Cocos nucifera* oil, *Butyrospermum parkii, Orbignya oleifera, Mangifera indica, Irvingia gabonensis* kernel butter, *Hordeum vulgare, Argania spinosa, Melia azadirachta, Hydnocarpus kurzii, Nigella sativa, Humulus lupulus strobili, Coffea arabica* seed oil, *Brassica campestris* sterols, *Lupinus albus* seed extract, oleic/linoleic/linolenic polyglycerides, *Arachis hypogaea, Daucus carota* sativa, β-caroten, *Passiflora incarnate* oil, *Boswellia serrata* gum, palmitoyl glycine, *Eucalyptus maculata citriodora* extract, p-menthane 3,8-diol, ethyl butylacetylaminopropionate, *Hypericum perforatum* oil, *Plea europaea, Centella asiatica,* and *Isochrysis galbana* extract;
d) at least one preservative, selected from the group consisting of caprylyl glycol, o-cymen-5-ol, and propylparaben; and
e) at least one powder, selected from the group consisting of glass beads, polymethyl methacrylate, silica, ethylene acrylic acid copolymer, nylon-10/10, talc, mica, *Oryza sativa* powder, synthetic fluorphlogopite, acrylates octylacrylamide copolymer, boron nitride, polyamide-5, aluminum starch octenylsuccinate, silica silylate, silica dimethyl silylate, cerium dioxide, lauryl methacrylate/glycol dimethacrylate crosspolymer, *Zea mays* starch, *Oryza sativa* starch, *Avena sativa* kernel flour, magnesium aluminum silicate, phospholipids, polyethylene, beads/granules from natural or synthetic origin, cellulose, hydroxyethylcellulose, and hydroxypropylcellulose.

Embodiments of the invention include a method of protecting skin from sunlight, comprising applying a sunscreen composition to skin, wherein the sunscreen composition is any of the sunscreen compositions described herein.

In some embodiments, the sunscreen is applied on the skin when the skin is under water or when the skin is already wet.

In some embodiments the skin is dry or wet when the sunscreen composition is applied on the skin and wherein contact with water will not result in almost any release of the composition. Consequently, contact with water will not cause a significant loss of protection against harmful sun rays.

DESCRIPTION OF THE INVENTION

The present invention provides a new sunscreen composition and a use of this sunscreen composition with very high water and sweat resistance properties. Embodiments of the present invention include the use of an 100% anhydrous sunscreen product, which can be applied on a wet skin, either in the presence of water by repelling water or water droplets respectively or in under-water conditions, which further provides a non-greasy feel, a very rapid spreadability, zero stickiness, and at the same time improves skin aspect (reduction of shine, optical reduction of fine lines and wrinkles). In comparison with conventional sunscreen products, the sunscreen of the present invention and its use differ regarding the fact that the latter can be applied on the skin in under-water and/or in-water conditions. The new sunscreen product of the present invention gets strongly anchored on the skin. Thus, the sunscreen as disclosed in the present invention enables the consumer to get in contact with water during or/and directly after application, or even apply it in the water/sea, etc., while swimming. For an improved convenience the sunscreen product of the present invention is not transparent. The sunscreen should be visible on the skin when the skin is under water. It helps the consumer to see easily where the product is applied and where is not. The non-transparent effect is accomplished by adding any favourable and compatible colour to the formulas.

The present invention provides the use of a sunscreen composition with SPF >=50 or 50 or 30 or <30 or according to any Sun Protection Factor that conforms to any current cosmetic legislation comprising a silicone organic elastomer blend and a silicone elastomer, wherein the silicone organic elastomer blend comprises Dimethicone/Bis-Isobutyl PPG-20 Crosspolymer in Isododecane in a concentration range from about 30% to about 90% w/w, wherein the silicone elastomer comprises Dimethicone/Vinyl Dimethicone Crosspolymer and Silica in a concentration range from about 0.1% to about 10% w/w, and wherein the sunscreen is applied on the skin in the presence of water.

The present invention provides the use of the sunscreen composition, wherein the sunscreen is applied on the skin when the skin is under water or when the skin is already wet by repelling water or water droplets.

The present invention further provides the use of the sunscreen composition, wherein the skin can come into contact with water directly after the sunscreen composition is applied on the skin.

The following composition provides a 100% anhydrous sunscreen product which is preferably composed by the combination of:

1. A silicone organic elastomer blend (SOEB), comprising Dimethicone/Bis-Isobutyl PPG-20 Crosspolymer and Isododecane; the silicone organic elastomer blend may be present in a concentration range from about 30% to about 90% w/w, preferably in a concentration range from about 55% to 65% w/w, Within this concentration range the concentration of 60,545% w/w has been shown to be the most favorable.
2. A silicone elastomer [SE] in powder form, comprising Dimethicone/Vinyl Dimethicone Crosspolymer and Silica; the silicone elastomer may be present in a concentration range from about 0.1% to about 10% w/w, preferably in a concentration range from about 0,5% to 1,5% w/w. Within this concentration range the concentration of 1% w/w has been shown to be the most favorable.
3. An effective oil soluble and liquid UV-B absorber, comprising octocrylene, at a proportion dependable on the desired SPF.
4. An effective UV-B absorber with additional absorption effect in the short-wave UV-A range, comprising ethylhexyl methoxycinnamate, at a proportion dependable on the desired SPF.
5. An effective organic UV-A absorber, comprising diethylamino hydroxybenzoyl hexyl benzoate, at a proportion dependable on the desired SPF.
6. An effective UV-B absorber, comprising ethylhexyl salicylate, at a proportion dependable on the desired SPF.
7. An oily component for emulsion cosmetic preparation, comprising dibutyl adipate; dependable on the effective solubilisation of the UV filters the oily component may be present in a concentration range from about 1% to about 20% w/w, particularly in a preferred concentration of about 5% w/w.
8. A Preservation enhancing agent that provides antimicrobial protection to the product itself, comprising caprylyl glycol, the preservation enhancing agent may be present in a concentration range from about 0.01% to about 1% w/w, particularly in a preferred concentration of about 0.6% w/w
9. Spherical glass beads, comprising soda lime, solid glass microspheres, preferably with a means size of 3.5-5.5 microns, dependable on the targeted wrinkle masking effect or/and heat dissipation effect the spherical glass beads may be present in a concentration range from about 0.1% to about 5% w/w, particularly in a preferred concentration of about 0.5% w/w
10. An Anti-inflammatory ingredient, comprising alpha bisabolol, the anti-inflammatory ingredient may be present in a concentration range of about 0.1% to about 1% w/w, particularly in a preferred concentration of about 0.5% w/w
11. An antioxidant and anti-aging component, comprising a mixture of active ingredients comprising ethyl ferulate, *Rosmarinus officinalis*, disodium uridine phosphate, polyglyceryl-5 trioleate, *Rosmarinus officinalis* extract, *Helianthus annuus* seed oil (trade name: Celligent®), the anti-aging component may be present in a concentration range of about 0.1% to about 5% w/w, particularly in a preferred concentration of about 0.5% w/w
12. Titanium dioxide and/or iron oxides either in the form of powders or in the form of dispersions in a proportion directly dependable on the targeted color of the end product, the titanium dioxide and/or iron oxides may be presented in a concentration range of about 0.01% to about 20% w/w, particularly in a preferred concentration range of about 0.025% to about 9% w/w
13. Perfume in a concentration range of about 0.00% to about 1% w/w, particularly in a preferred concentration of about 0.1% w/w.

Above mentioned silicone organic elastomer blend (SOEB) comprising Dimethicone/Bis-Isobutyl PPG-20 Crosspolymer which is combined to Isododecane is not restricted. In accordance with the present invention the Dimethicone/Bis-Isobutyl PPG-20 Crosspolymer can be combined with other materials apart from Isododecane including, without limitation, Cyclomethicone or Isohexadecane.

Above mentioned silicone elastomer (SE) in powder form comprising Dimethicone/Vinyl Dimethicone Crosspolymer which is treated and combined with Silica is not restricted. In accordance with the present invention the Dimethicone/Vinyl Dimethicone Crosspolymer can be treated and/or combined with other materials apart from Silica or has no special treatment.

The above mentioned UV-Filters are also not restricted. In accordance with the present invention UV-filters apart from those mentioned above that are useful include, without limitation, butyl methoxydibenzoylmethane, bis-ethylhexyloxyphenol methoxyphenyl triazine, isoamyl methoxycinnamate, homosalate, 4-methylbenzylidene camphor, titanium dioxide, zinc oxide, benzophenone-3 any other UV-filter approved by European or USA or any other official legislation and combinations thereof.

The required % w/w of the UV-filters is proved every time by in vivo and/or in vitro SPF and UVA studies, those are performed always according to the requirements of the currently existing Legislation (i.e. EU Regulations 76/768/ECC and EC 1223/2009) or any future ones.

In some embodiments, active agents may include, without limitation, *Crambe maritima*, *Bixa orellana*, retinyl palmitate, tocopheryl acetate, ascorbyl tetraisopalmitate, *Pistacia lentiscus* gum, *Salicornia herbacea* extract, *Rasa moschata* seed oil, teprenone, *Serenoa serrulate*, butyl avocadate, dipalmitoyl hydroxyproline, *Glycine soja* seed oil, ceramide-2, *Zea mays* oil, *Crambe abyssinica* seed oil phytosterol esters, *Echium plantagineum* seed oil, *Cardiospermum halicacabum* flower/leaf/vine extract, phytosphingosine, *Helianthus annuus* seed oil unsaponifiables, sodium caproyl/lauryl lactylate, triethyl citrate, *Salvia officinalis* oil, kojic acid dipalmitate, lecithin, arachidyl propionate, ethyl linoleate, ethyl linolenate, ethyl oleate, bakuchiol, *Juglans regia*, *Sesamum indicum* oil, *Triticum vulgare* germ oil, *Arnica montana*, *Cupressus sempervirens*, *Polygonatum multiflarum*, *Cocas nucifera* oil, *Butyrospermum parkii*, *Orbignya oleifera*, *Mangifera indica*, *Irvingia gabonensis* kernel butter, *Hordeum vulgare*, *Argania spinosa*, *Coelia azadirachta*, *Hydnocarpus kurzii*, *Nigella sativa*, *Humulus lupulus strobili*, *Coffea arabica* seed oil, *Brassica campestris* sterols, *Lupinus albus* seed extract, oleic/linoleic/linolenic polyglycerides, *Arachis hypogaea*, *Daucus carota sativa*, β-caroten, *Passiflora incarnata* oil, *Boswellia serrata* gum, palmitoyl glycine, *Eucalyptus maculata citriodora* extract, p-menthane 3,8-diol, ethyl butylacetylaminopropionate, *Hypericum perforatum* oil, *Plea europaea*, *Centella asiatica*, *Isochrysis galbana* extract and combinations thereof.

In some embodiments, oily components may include, without limitation, phenethyl benzoate, caprylic/capric triglyceride, C12-15 alkyl benzoate, PPG-3 benzyl ether myristate, C12-13 alkyl lactate, isodecyl salicylate, Di-C12-13 alkyl malate, isoamyl laurate, propylheptyl caprylate, butyloctyl salicylate, polycrylene, dicaprylyl carbonate, dicaprylyl ether, 2-octyldodecylmyristate, isohexadecane, dimethyl capramide, *Crambe abyssinica* oil, squalene, rice bran/germ oil, *Helianthus annuus* seed oil, *Ricinus communis* oil, dimethicone, cyclomethicone, caprylyl methicone, dimethicone copolyol, undecylcrylene dimethicone, isopropyl isostearate, isostearyl isostearate, octyldodecanol, cocaglycerides, C13-15 Alkane, C15-19 Alkane, C17-23 Alkane, C21-Alkane, propylene glycol dipelargonate, diisopropyl sebacate, isononyl isononanoate, isocetyl stearoyl stearate, dipentaerithrityl hexacaprylate/hexacaprate, isodecyl neopentanoate, natural essential oils and combinations thereof.

In some embodiments, preservation enhancing agents may include, without limitation o-cymen-5-ol, propylparaben and combinations thereof.

In some embodiments, powder agents apart from spherical glass beads may include, without limitations, polymethyl methacrylate, silica, ethylene acrylic acid copolymer, nylon-10/10, talc, mica, *Oryza sativa* powder, synthetic fluorphlogopite, acrylates/octylacrylamide copolymer, boron nitride, polyimide-5, aluminum starch octenylsuccinate, silica silylate, silica dimethyl silylate, cerium dioxide, lauryl methacrylate glycol dimethacrylate crosspolymer, *Zea mays* starch, *Oryza sativa* starch, *Avena sativa* kernel flour, magnesium aluminum silicate, phospholipids, polyethylene, beads/granules from natural or synthetic origin, cellulose, hydroxyethylcellulose, hydroxypropylcellulose and combinations thereof.

In accordance with the present invention, the sunscreen product could have in parallel some secondary properties, based on specially selected raw materials. Examples of these secondary properties could be without limitations:

Moisturizing
Antiageing (including claims like: photoageing, hormonal ageing, infra-red ageing, inflammaging etc.)
Anti-wrinkle
Antioxidant and/or cells' DNA protection and/or cells' DNA repair and/or detoxifying and/or anti-stress and/or antipollution
Seboregulating
Antimicrobial
Epidermal barrier strengthening and/or skin protection (referring to normal and extreme conditions eg. snow, high altitude, seaside conditions with high humidity and increased radiation etc.)
Healing
Anti-inflammatory
Rejuvenating and/or restructuring
Foundations and/or covering/coloring skin imperfections (BB, CC, DD, EE product types)
Mattifying
Primer
Lipolytic/slimming/anti-cellulite
Firming
Draining
Remodeling and/or face/body sculpturing
Microcirculation improving
Capillaries' enhancing
Insect repellent
Tan accelerating and/or tan prolonging
Self tan
Whitening and/or lightening
Hair retardation
Hair enhancement
Antiperspirant and/or deodorant and/or odour masking
Exfoliating and/or keratolytic and/or keratoplastic In some embodiments, the sunscreen products are in various forms depending on the viscosity of the end product (fluctuating from sprayable liquid forms to thick gels).

The Manufacturing Method of the Product:

In the $1^{st}$ phase (I) the selected % w/w of SOEB is weighed and placed in the main production vessel and heated up to a maximum of 40° C. under mild planetary agitation in order to evaporate as more as possible the volatile fractions of it, which—in case they are not condensated enough at this specific point of the production procedure—might cause eye irritation (eg. lacrimation) during the application of the end product on the skin of the face.

In the $2^{nd}$ phase (II) the selected % of the organic UVB & UVA filters and the oily components like emollient esters (eg. dibutyl adipate) are weighed and placed into the auxiliary production vessel, heated up to 80° C. till the complete dissolution of the solid materials and following they are cooled down slowly to 40° C.

In the $3^{rd}$ phase (III) when the mixture of phase (II) reaches 40° C., it is added into the bulk of phase (I) under intense homogenization (1.000-10.000 rpm). After the mix-up of the phases (I) and (II), a special combination of mechanical equipment is used in order to homogenize the bulk very intensively and thus to capture phase (H) as good as possible into the network of the SOEB. This special equipment decreases the diameter of the captured phase micelles, improving product's aspect and functionality. The intensive homogenization is performed at the same high rpm till the bulk's aspect is completely homogeneous, preferably for 1 hour.

In the homogenized product of phase (III) there are added the rest of the raw materials (emollients, silicones, active ingredients, preservation enhancing agents and colors) always at the same high rpm (1.000-10.000 rpm).

If the colors are in powder form, they are preferred to be added in phase I in order to be captured in the SOEB network.

Following, the selected % w/w of the silicon elastomer in powder form is added and it is homogenized for approximately 30 minutes at the same rpm (1,000-10,000 rpm). Finally, there are added all the remained selected powders and the product is being homogenized preferably (but not restricted) for approximately 1 hour under cooling in order to avoid any possible overheating. The bulk is cooled down slowly to 28° C. During the manufacturing procedure, the addition of the active ingredients or/and the preservation enhancing agents may take place even after the addition of the silicon elastomer in powder form or the rest of the selected powders. The criteria for this slight process modification are the nature and the properties of the selected active ingredients and the preservation enhancing agents.

Some embodiments of the invention overcome the disadvantages described in the opening part "background of the invention". Some embodiments may be described as Under-Water-Technology, to describe the ability of the sunscreen to get in contact with water during its application or right before or right after its application on the skin without diluting.

In embodiments, the sunscreen product may be applied on the skin
- When the consumer is under water (meaning when he is in the sea or in the pool etc.)
- When the consumer has wet skin (e.g. when he has just came out of the water, or he is sweating due to exposure in warm temperatures or due to sport activities, etc.)
- When the consumer is just about to enter the water and get in contact with water extremely soon after the application of the product (in the following seconds or minutes)

This new technology helps the sunscreen product to get quickly anchored onto the wet skin, even in under-water conditions, as if the skin was dry. While being applied on the skin, it repels water and it gets strongly anchored leading to increased skin protection and reduced environmental burden.

Further, this new technology reassures the UV-filter compounds and/or the UV-screening compounds will not to be diluted; it helps the sunscreen product to be easily applied, not to smear, not to form any white/pasty/incomplete film and to provide sufficient protection against UV radiation.

EMBODIMENTS

The following examples are supposed to show how the invention can be carried out. For the manufacture of the appropriate products described in the subsequent examples, there is followed the process that is described above during the analysis of the production method.

Example 1

Composition of a 100% anhydrous colored sunscreen product SPF50+ with Under Water Technology:

The followed embodiment discloses beside the chemical names also usual trade names, which are not restricted but rather are taken as an example.

| % w/w | Component/INCI Name | Trade Name |
|---|---|---|
| 60.545 | Isododecane and Dimethicone/Bis-Isobutyl PPG-20 Crosspolymer | Dow Corning ® EL 8050 ID |
| 10 | Octocrylene | NEO Heliopan ® 303/Escalol 597 |
| 8.5 | Ethylhexyl Methoxycinnamate | Heliovisor OMC/Escalol 557 |
| 8 | Diethylamino Hydroxybenzoyl Hexyl Benzoate | Uvinul A Plus |
| 5 | Ethylhexyl Salicylate | Heliovisor OSA |
| 5 | Dibutyl Adipate | Saboderm DBA |
| 0.6 | Caprylyl Glycol | Dermosoft Octiol |
| 1 | Dimethicone/Vinyl Dimethicone Crosspolymer and Silica | Dow Corning ® 9701 |
| 0.5 | Glass Beads | Prizmalite Glass Beads P2011SL |
| 0.5 | Bisabolol | Alpha Bisabolol Natural Brazil-102026 |
| 0.1 | Active ingredients based on inter alia sunflower oil, ethyl ferulate, disodium uridine phosphate and rosemary Extract | Celligent ® |
| 0.025 | Iron oxides (CI 77492 and CI 77491 and CI 77499 in *ricinus communis* oil) | Brun Covapate W 8768 |
| 0.05 | Yellow 5 (CI 19140 in *ricinus communis* oil) | Jaune Covapate W 1761 |
| 0.08 | Titanium Dioxide (CI 77891 in *ricinus communis* oil) | Blanc Covapate W 9765 |
| 0.1 | Parfum | Perfume 'OKADI SUN' FC 10523/1 |

Example 2

| % w/w | Chemical Component/INCI Name |
|---|---|
| 57.745 | Isododecane and Dimethicone/Bis-Isobutyl PPG-20 Crosspolymer |
| 8 | Octocrylene |
| 10 | Homosalate |
| 5 | Benzophenone 3 |
| 3 | Butyl Methoxydibenzoylmethane |
| 5 | Butyloctyl Salicylate |
| 4 | Ethylhexyl Methoxycrylene |
| 5 | Dibutyl Adipate |
| 0.5 | Caprylyl Glycol |
| 1 | Dimethicone/Vinyl Dimethicone Crosspolymer and Silica |
| 0.5 | Glass Beads |
| 0.1 | Active ingredients based on inter alia sunflower oil, ethyl ferulate, disodium uridine phosphate and rosemary extract (Celligent ®) |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |

Example 3

| % w/w | Chemical Component/INCI Name |
|---|---|
| 59.245 | Isododecane and Dimethicone/Bis-Isobutyl PPG-20 Crosspolymer |
| 10 | Octocrylene |
| 5 | Benzophenone 3 |
| 3 | Butyl Methoxydibenzoylmethane |
| 7.5 | Ethylhexyl Methoxycinnamate |
| 5 | Ethylhexyl Salicylate |
| 8 | Dibutyl Adipate |
| 0.5 | Caprylyl Glycol |
| 0.5 | Dimethicone/Vinyl Dimethicone Crosspolymer and Silica Glass Beads |
| 0.1 | Active ingredients based on inter alia sunflower oil, ethyl ferulate, disodium uridine phosphate and rosemary extract (Celligent ®) |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |

Example 4

| % w/w | Chemical Component/INCI Name |
|---|---|
| 50.9 | Isododecane and Dimethicone/Bis-Isobutyl PPG-20 Crosspolymer |
| 10 | Octocrylene |
| 5 | Benzophenone 3 |
| 3 | Butyl Methoxydibenzoylmethane |
| 7.5 | Ethylhexyl Methoxycinnamate |
| 5 | Ethylhexyl Salicylate |
| 8 | Dibutyl Adipate |
| 0.5 | Caprylyl Glycol |
| 1 | Dimethicone/Vinyl Dimethicone Crosspolymer and Silica |
| 0.1 | Glass Beads |
| 0.1 | Active ingredients based on inter alia sunflower oil, ethyl ferulate, disodium uridine phosphate and rosemary extract (Celligent ®) |
| 0.2 | Iron oxides CI 77499 (and) Isopropyl e Titanium Triisostearat |
| 0.9 | Iron oxides CI 77492 (and) Isopropyl Titanium Triisostearate |
| 0.3 | Iron oxides CI 77491 (and) Isopropyl Titanium Triisostearate |
| 7.5 | Titanium Dioxide (and) Isopropyl Titanium Triisostearate |

Example 5

| % w/w | Component/INCI Name |
|---|---|
| 59.545 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 0.5 | Bisabolol |
| 0.1 | *Salicornia Herbacea* Extract |
| 1 | Di-C12-13 Alkyl Malate |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 6

| % w/w | Component/INCI Name |
|---|---|
| 60.945 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 0.2 | *Pistacia Lentiscus* Gum |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 7

| % w/w | Component/INCI Name |
|---|---|
| 60.945 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 0.2 | Palmitoyl Glycine |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 8

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |

-continued

| % w/w | Component/INCI Name |
|---|---|
| 0.6 | Caprylyl Glycol |
| 1 | Dimethicone/Vinyl Dimethicone Crosspolymer and Silica |
| 0.5 | Glass Beads |
| 1 | Ascorbyl Tetraisopalmitate |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 9

| % w/w | Component/INCI Name |
|---|---|
| 60.945 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 0.2 | Bakuchiol |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 10

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | *Hydnocarpus Kurjii* |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 11

| % w/w | Component/INCI Name |
|---|---|
| 59.145 | Isododecane and Dimethicone/Bis-Isobutyl PPG-20 Cross polymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | *Zea Mays* Oil |
| 1 | *Passiflora Incarnata* |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 12

| % w/w | Component/INCI Name |
|---|---|
| 59.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | Retinyl Palmitate |
| 1 | *Centella Asiatica* |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 13

| % w/w | Component/INCI Name |
|---|---|
| 59.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 2 | Mixture of *Helianthus Annuus* Seed Oil, *Echium Plantagineum* Seed Oil, *Cardiospermum Halicacabum* Flower/Leaf/Vine Extract and Octyldodecanol |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 14

| % w/w | Component/INCI Name |
|---|---|
| 59.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 2 | Mixture of *Coffea Arabica* Seed Oil and *Brassica Campestris* Sterols |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 15

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | Mixture of *Lupinus Albus* Extract and *Helianthus Annuus* Seed Oil |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 16

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | *Hypericum Perforatum* Oil |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 17

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | Mixture of *Mentha Arvensis* Leaf Oil, *Citrus Medica Limonum* Peel Oil, *Cupressus Sempervirens* Oil, *Lavandula Hybrida* Oil and *Cistus Ladaniferus* Oil |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 18

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | *Eucalyptus Maculata Citriodora* Extract |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 19

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | *Juglans Regia* |
| 0.025 | Iron oxides (CI 77492 and CI 77491 and CI 77499 in *ricinus communis* oil) |

-continued

| % w/w | Component/INCI Name |
|---|---|
| 0.05 | Yellow 5 (CI 19140 in *ricinus communis* oil) |
| 0.08 | Titanium Dioxide (CI 77891 in *ricinus communis* oil) |
| 0.1 | Parfum |

Example 20

| % w/w | Component/INCI Name |
|---|---|
| 60.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 1 | Mixture of *Isochrysis Galbana* Extract and Caprylic/Capric Triglyceride |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

Example 21

| % w/w | Component/INCI Name |
|---|---|
| 58.145 | Isododecane and Dimethicone/Bis-Isobutyl PPG-20 Crosspolymer |
| 10 | Octocrylene |
| 8.5 | Ethylhexyl Methoxycinnamate |
| 8 | Diethylamino Hydroxybenzoyl Hexyl Benzoate |
| 5 | Ethylhexyl Salicylate |
| 5 | Dibutyl Adipate |
| 0.6 | Caprylyl Glycol |
| 1 | Dimethicone/Vinyl Dimethicone Crosspolymer and Silica |
| 0.5 | Glass Beads |
| 3 | Mixture of *Humulus Lupulus* Strobile and Caprylic/Capric Triglyceride |
| 0.025 | Iron oxides (CI 77492 and CI 77491 and CI 77499 in *ricinus communis* oil) |
| 0.05 | Yellow 5 (CI 19140 in *ricinus communis* oil) |
| 0.08 | Titanium Dioxide (CI 77891 in *ricinus communis* oil) |
| 0.1 | Parfum |

The invention claimed is:

1. A method for applying an anhydrous sunscreen composition, said sunscreen having an SPF >=50, 50, 30, or <30, wherein the sunscreen comprises a silicone organic elastomer blend and a silicone elastomer, wherein the silicone organic elastomer blend comprises Dimethicone/Bis-Isobutyl PPG-20 Crosspolymer in Isododecane in a concentration range from about 30% to about 90% of total weight of the composition, wherein the silicone elastomer comprises Dimethicone/Vinyl Dimethicone Crosspolymer and Silica in a concentration range from about 0.1% to about 10% of total weight of the composition, wherein the sunscreen further comprises spherical glass beads comprising soda lime, solid glass microspheres with a mean size of 3.5-5.5 microns, wherein the method comprises:
applying the sunscreen on skin that is underwater.

2. The method of claim 1, further comprising conducting a subsequent application step of the sunscreen composition when the skin is wet from being under water, wherein the application step repels water or water droplets.

3. The method of claim 2, wherein the skin can come into contact with water directly after the sunscreen composition is applied in the subsequent application step.

4. The method of claim 1, wherein the Dimethicone/Bis-Isobutyl PPG-20 Crosspolymer in Isododecane is present in a concentration range from about 55% to about 65% of total weight of the composition, and wherein the Dimethicone/Vinyl Dimethicone Crosspolymer and Silica is present in a concentration range from about 0.5% to about 1.5% of total weight of the composition.

5. The method of claim 1, wherein the Dimethicone/Bis-Isobutyl PPG-20 Crosspolymer in Isododecane is present in a concentration about 60.545% of total weight of the composition and wherein the Dimethicone/Vinyl Dimethicone Crosspolymer and Silica is present in a concentration about 1% of total weight of the composition.

6. The method of claim 1, wherein the silicone organic elastomer blend comprises Dimethicone/Bis-Isobutyl PPG-20 Crosspolymer in Isohexadecane.

7. The method of claim 1, wherein the composition further comprises organic or/and inorganic UVA & UVB-filters in a concentration range from about 10% to about 50% of total weight of the composition directly dependable to the targeted SPF.

8. The method of claim 7, wherein the UVA-filter is selected from a group consisting of Diethylamino Hydroxybenzoyl Hexyl Benzoate, Butyl Methoxydibenzoylmethane, Bis-Ethylhexyloxyphenol Methoxyphenyl Triazine, and Benzophenone-3 in a ratio directly relatable to the targeted SPF.

9. The method of claim 7, wherein the UVB-filter is selected from a group consisting of Octocrylene, Ethylhexyl Methoxycinnamate, Ethylhexyl Salicylate, Isoamyl Methoxycinnamate, and Homosalate.

10. The method of claim 7, wherein Octocrylene, Ethylhexyl Methoxycinnamate and/or Ethylhexyl Salicylate are used as UVB-filter in a ratio directly relatable to the targeted SPF.

11. The method of claim 7, wherein Diethylamino Hydroxybenzoyl Hexyl Benzoate is used as UVA-filter in a ratio directly dependable to the targeted SPF.

12. The method of claim 1, wherein the composition further comprises iron oxides, yellow 5 and/or titanium dioxide.

13. The method of claim 12, wherein the iron oxides, yellow 5 and/or titanium dioxide are selected from a group consisting of CI 77492, CI 77491, CI 77499 in *Ricinus communis* oil, CI 19140 in *Ricinus communis* oil, and CI 77891 in *Ricinus communis* oil.

14. The method of claim 12, wherein the iron oxides and/or titanium dioxide are selected from a group consisting of iron oxides CI 77499 (and) isopropyl titanium triisostearate, iron oxides CI 77492 (and) isopropyl titanium triisostearate, iron oxides CI 77491 (and) isopropyl titanium triisostearate, titanium dioxide, and isopropyl titanium triisostearate.

15. The method of claim 1, wherein the composition further comprises at least one member which is selected from each of the groups a), b), c), d) and e), wherein:

a) is at least one emollient ester selected from the group consisting of dibutyl adipate, phenethyl benzoate, caprylic/capric triglyceride, C12-15 alkyl benzoate, PPG-3 benzyl ether myristate, C12-13 alkyl lactate, isodecyl salicylate, Di-C12-13 alkyl malate, isoamyl laurate, propylheptyl caprylate, butyloctyl salicylate, polycrylene, dicaprylyl carbonate, dicaprylyl ether, 2-octyldodecylmyristate, isohexadecane, dimethyl capramide, *Crambe abyssinica* oil, squalene, rice bran/germ oil, *Helianthus annuus* seed oil, *Ricinus communis* oil, dimethicone, cyclomethicone, caprylyl methicone, dimethicone copolyol, undecylcrylene dimethicone, isopropyl isostearate, isostearyl isostearate, octyldodecanol, coco-glycerides, C13-15 Alkane, C15-19 Alkane, C17-23 Alkane, C21-28 Alkane, propylene glycol dipelargonate, diisopropyl sebacate, isononyl isononanoate, isocetyl stearoyl stearate, dipentaerithrityl hexacaprylate/hexacaprate, isodecyl neopentanoate, and natural essential oils;

b) is at least one anti-aging ingredient selected from the group consisting of ethyl ferulate, *Rosmarinus officinalis*, disodium uridine phosphate, polyglyceryl-5 trioleate, *Rosmarinus officinalis* extract, and *Helianthus annuus* seed oil;

c) is at least one active ingredient, selected from a group consisting of a-bisabolol, *Crambe maritima, Bixa orellana*, retinyl palmitate, tocopheryl acetate, ascorbyl tetraisopalmitate, *Pistacia lentiscus* gum, *Salicornia herbacea* extract, *Rosa moschata* seed oil, teprenone, *Serenoa serrulata*, butyl avocadate, dipalmitoyl hydroxyproline, *Glycine soja* seed oil, ceramide-2, *Zea mays* oil, *Crambe abyssinica* seed oil phytosterol esters, *Echium plantagineum* seed oil, *Cardiospermum halicacabum* flower/leaf/vine extract, phytosphingosine, *Helianthus annuus* seed oil unsaponifiables, sodium caproyl/lauryl lactylate, triethyl citrate, *Salvia officinalis* oil, kojic acid dipalmitate, lecithin, arachidyl propionate, ethyl linoleate, ethyl linolenate, ethyl oleate, bakuchiol, *Juglans regia, Sesamum indicum* oil, *Triticum vulgare* germ oil, *Arnica montana, Cupressus sempervirens, Polygonatum multiflorum, Cocos nucifera* oil, *Butyrospermum parkii, Orbignya oleifera, Mangifera indica, Irvingia gabonensis* kernel butter, *Hordeum vulgare, Argania spinosa, Melia azadirachta, Hydnocarpus kurzii, Nigella sativa, Humulus lupulus strobili, Coffea arabica* seed oil, *Brassica campestris* sterols, *Lupinus albus* seed extract, oleic/linoleic/linolenic polyglycerides, *Arachis hypogaea, Daucus carota sativa*, β-caroten, *Passiflora incarnata* oil, *Boswellia serrata* gum, palmitoyl glycine, *Eucalyptus maculata citriodora* extract, p-menthane 3,8-diol, ethyl butylacetylaminopropionate, *Hypericum perforatum* oil, *Olea europaea, Centella asiatica*, and *Isochrysis galbana* extract;

d) is at least one preservative selected from a group consisting of caprylyl glycol, o-cymen-5-ol, and propylparaben; and e) is at least one powder selected from a group consisting of glass beads, polymethyl methacrylate, silica, ethylene acrylic acid copolymer, nylon-10/10, talc, mica, *Oryza sativa* powder, synthetic fluorphlogopite, acrylates/octylacrylamide copolymer, boron nitride, polyamide-5, aluminum starch octenylsuccinate, silica silylate, silica dimethyl silylate, cerium dioxide, lauryl methacrylate/glycol dimethacrylate crosspolymer, *Zea mays* starch, *Oryza sativa* starch, *Avena sativa* kernel flour, magnesium aluminum silicate, phospholipids, polyethylene, beads/granules from natural or synthetic origin, cellulose, hydroxyethylcellulose, and hydroxypropyl cellulose.

16. A sunscreen comprising a silicone organic elastomer blend and a silicone elastomer, wherein the silicone organic elastomer blend consists of Dimethicone/Bis-Isobutyl PPG-20 Crosspolymer in Isododecane in a concentration range from about 55% to about 65% of total weight of the composition, wherein the silicone elastomer comprises Dimethicone/Vinyl Dimethicone Crosspolymer and Silica in a concentration range from about 0.1% to about 10% of total weight of the composition, and wherein the sunscreen further comprises spherical glass beads comprising soda lime, solid glass microspheres with a mean size of 3.5-5.5 microns.

17. The method of claim 1, wherein the sunscreen composition is visible under water.

18. The sunscreen of claim 16, wherein the sunscreen is visible under water.

* * * * *